(12) United States Patent
Biadillah et al.

(10) Patent No.: US 9,442,046 B2
(45) Date of Patent: Sep. 13, 2016

(54) DEVICE FOR SAMPLE COLLECTION

(75) Inventors: Youssef Biadillah, Lausanne (CH);
Stephen Douglas Andrews, Falmouth, ME (US)

(73) Assignee: AboGen, Inc., Portland, ME (US)

( * ) Notice: Subject to any disclaimer, the term of this patent is extended or adjusted under 35 U.S.C. 154(b) by 0 days.

(21) Appl. No.: 14/127,832

(22) PCT Filed: Jun. 19, 2012

(86) PCT No.: PCT/US2012/043176
§ 371 (c)(1),
(2), (4) Date: Dec. 19, 2013

(87) PCT Pub. No.: WO2012/177656
PCT Pub. Date: Dec. 27, 2012

(65) Prior Publication Data
US 2014/0120531 A1 May 1, 2014

Related U.S. Application Data

(60) Provisional application No. 61/598,601, filed on Feb. 14, 2012, provisional application No. 61/598,618, filed on Feb. 14, 2012, provisional application No. 61/498,584, filed on Jun. 19, 2011.

(51) Int. Cl.
*G01N 33/00* (2006.01)
*G01N 1/10* (2006.01)
(Continued)

(52) U.S. Cl.
CPC .............. *G01N 1/10* (2013.01); *A61B 10/007* (2013.01); *A61B 10/0051* (2013.01);
(Continued)

(58) Field of Classification Search
CPC ...... G01N 1/10; A61B 10/51; B01L 2300/47
See application file for complete search history.

(56) References Cited

U.S. PATENT DOCUMENTS 5,478,722 A 12/1995 Caldwell
6,582,415 B1 6/2003 Fowles et al.
(Continued)

FOREIGN PATENT DOCUMENTS

JP S63-070954 U 5/1988
JP H09-500723 A 1/1997
(Continued)

OTHER PUBLICATIONS

International Search Report for International Application No. PCT/US2012/043176, mailed Feb. 26, 2013.
(Continued)

*Primary Examiner* — Sam P Siefke
(74) *Attorney, Agent, or Firm* — Cooley LLP

(57) ABSTRACT

The disclosure relates to devices, solutions and methods for collecting and processing samples of bodily fluids containing cells (as well as embodiments for the collection, and processing and/or analysis of other fluids including toxic and/or hazardous substances/fluids). In addition, the disclosure relates generally to function genomic studies and to the isolation and preservation of cells from saliva and other bodily fluids (e.g., urine), for cellular analysis. With respect to devices for collection of bodily fluids, some embodiments include two mating bodies, a cap and a tube (for example), where, in some embodiments, the cap includes a closed interior space for holding a sample preservative solution and mates with the tube to constitute the (closed) sample collection device. Upon mating, the preservation solution flows into the closed interior space to preserve cells in the bodily fluid. The tube is configured to receive a donor sample of bodily fluid (e.g., saliva, urine), which can then be subjected to processing to extract a plurality of cells. The plurality of cells can be further processed to isolate one and/or another cell type therefrom. The plurality of cells, as well as the isolated cell type(s), can be analyzed for functional genomic and epigenetic studies, as well as biomarker discovery.

14 Claims, 9 Drawing Sheets

(51) Int. Cl.
  *A61B 10/00* (2006.01)
  *B01L 3/00* (2006.01)
  *G01N 1/00* (2006.01)

(52) U.S. Cl.
  CPC .......... *A61B 10/0096* (2013.01); *B01L 3/502* (2013.01); *B01L 3/5021* (2013.01); *B01L 3/50825* (2013.01); *B01L 2300/047* (2013.01); *B01L 2300/049* (2013.01); *B01L 2400/0683* (2013.01); *G01N 2001/002* (2013.01)

(56) References Cited

U.S. PATENT DOCUMENTS

| | | |
|---|---|---|
| 8,796,028 B2 | 8/2014 | Holländer |
| 2001/0023072 A1 | 9/2001 | Crawford et al. |
| 2003/0119077 A1 | 6/2003 | Ts'o et al. |
| 2004/0038424 A1 | 2/2004 | Maples |
| 2006/0280650 A1* | 12/2006 | Wong et al. .................. 422/58 |
| 2009/0216213 A1 | 8/2009 | Muir et al. |

FOREIGN PATENT DOCUMENTS

| | | |
|---|---|---|
| JP | 2002-156317 A | 5/2002 |
| JP | 2009-051555 A | 3/2009 |
| JP | 2009-522542 A | 6/2009 |
| WO | WO 94/29691 | 12/1994 |

OTHER PUBLICATIONS

International Search Report of PCT/US2012/043176 issued on Feb. 26, 2013.

* cited by examiner

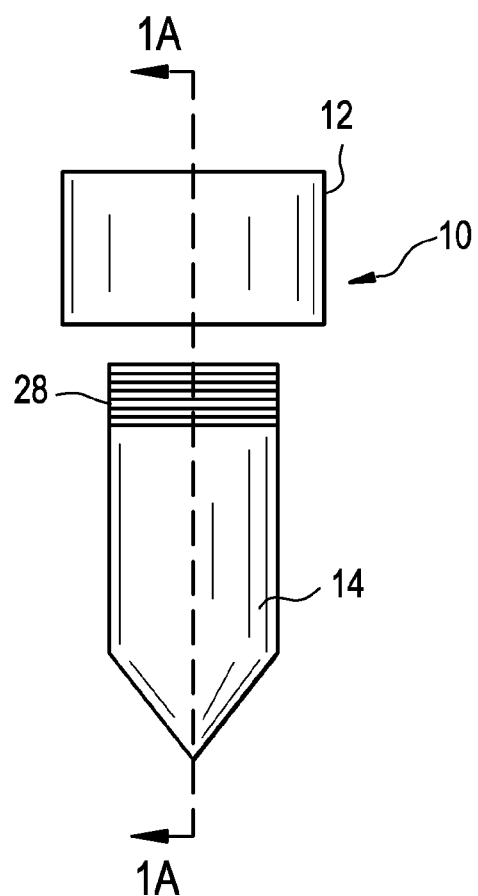

FIG. 2A
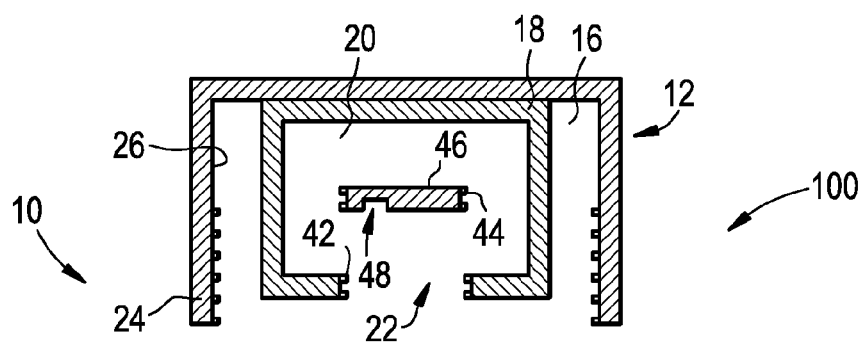
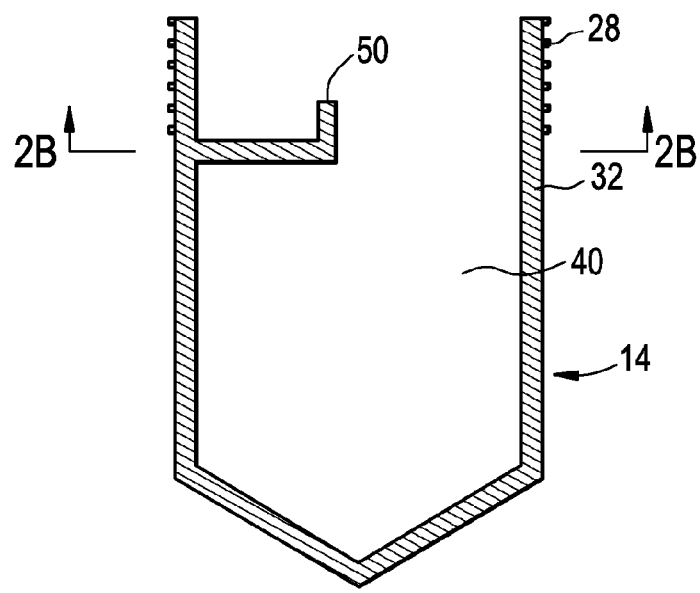
FIG. 2B
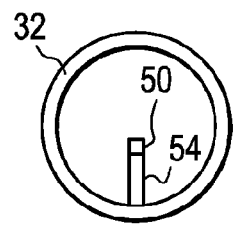

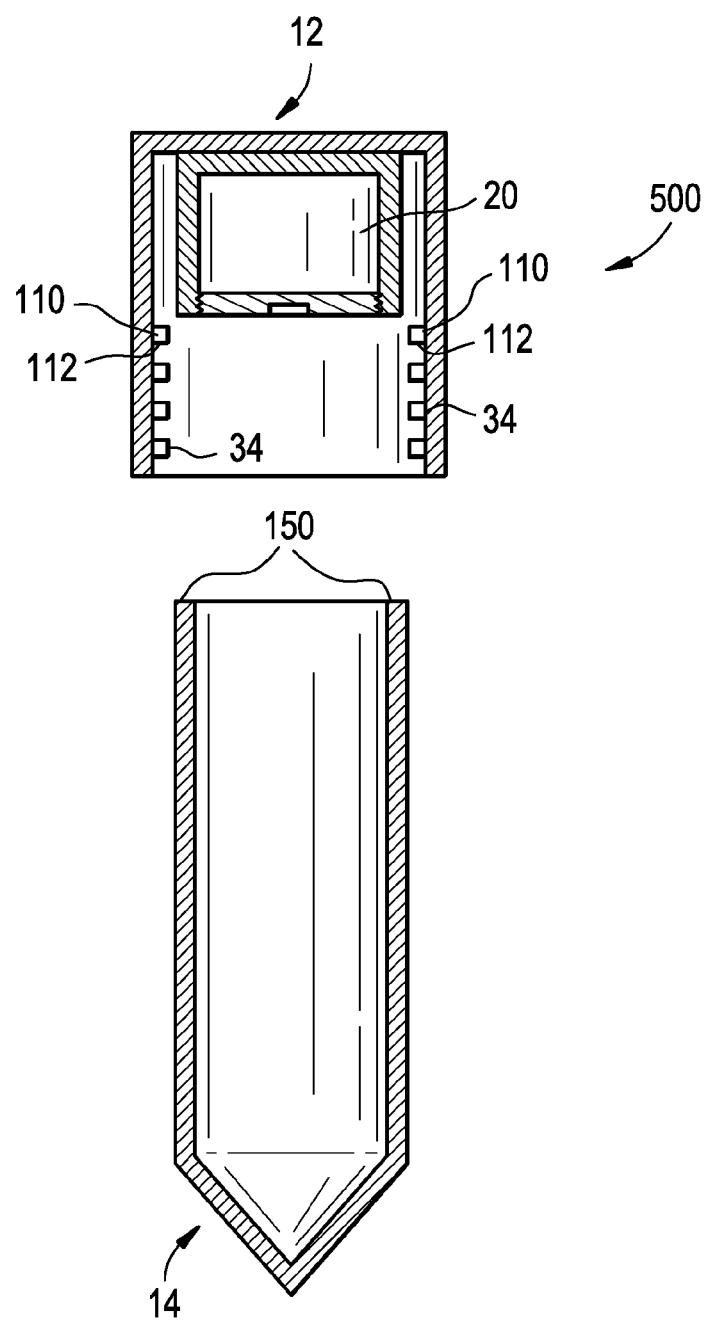

FIG. 7A
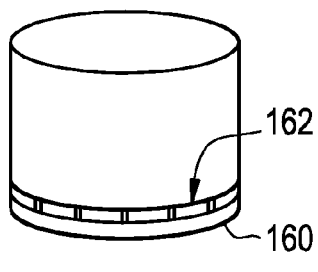
FIG. 7B
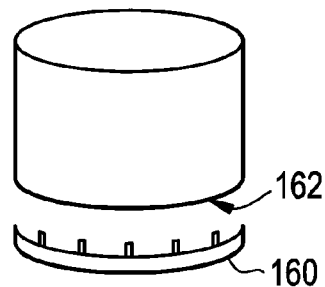
FIG. 8
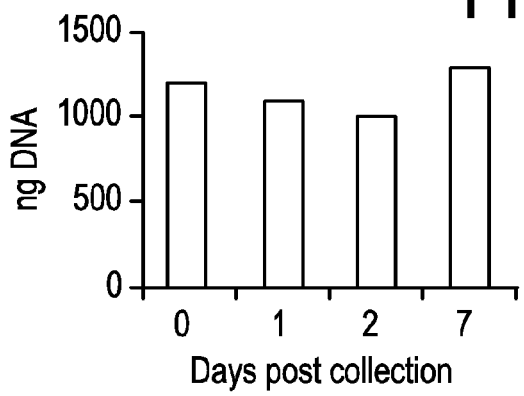
Time course of DNA yield of isolated T-cells after saliva samples stored in preservation solution at room temperature and then proceed.
DNA extracted from isolated T-cells after stored in preservation solution for indicated time.

Relative yield of extracted T-cells from saliva per ml of starting material compared to yield of T-cells from blood as determined By T-cell counting using light microscopy.

Saliva dose curve. Micrograms of isolated T-cell DNA per ml of starting saliva

DEVICE FOR SAMPLE COLLECTION

RELATED APPLICATIONS

The present application is a 35 U.S.C. §371 national stage entry of PCT/US2012/043176, having an international filing date of Jun. 19, 2012, which claims priority under 35 USC §119(e) to U.S. provisional patent application Nos. 61/498,584, filed Jun. 19, 2011, 61/598,601, filed Feb. 14, 2012, and 61/598,618, filed Feb. 14, 2012. Each of the foregoing disclosures is incorporated herein by reference in its entirety.

FIELD OF THE DISCLOSURE

The disclosure relates to devices, solutions and methods for collecting samples of bodily fluids or other substances, including hazardous and/or toxic substances, and in particular, a naturally expressed bodily fluid (e.g., saliva, urine). In addition, the disclosure relates generally to functional genomics and to the isolation and preservation of cells from such bodily fluids, for studies in any of: functional genomic and epigenetic studies, and biomarker discovery (for example).

BACKGROUND

Personalized medicine is the customization of treatment to an individual as opposed to the one treatment-for-all model. Personalized medicine involves categorizing a patient based on his or her physical condition and designing an optimal healthcare solution exclusively for that category. The progression of personalized medicine is dependent on the discovery, validation, and commercialization of biomarkers to stratify populations for treatment and for the development of diagnostics for screening and early detection.

Epigenetic research has come to the forefront of medical research and is implicated in the etiology of a number of physical and mental illnesses including: cancer, obesity, diabetes, schizophrenia, and Alzheimer's disease (Alika et al., 2010; Grant et al. 2010; McGowen et al., 2009; McGowen and Szyf, 2010; Plazas-Mayorca and Vrana, 2011; and Portela and Esteller, 2010). In addition, Epigenetics may hold particular promise in the many scientific and medical areas including but not limited to: cancer, diabetes, drug integrations, drug effectiveness, childhood aggression, suicidal behaviors, aging, inflammation, pain, obesity, schizophrenia, and other mental illnesses (Abdolmaleky et al., 2005; Costa et al., 2003; Iwamoto & Kato, 2009; Kuratomi et al., 2007; McGowan & Kato, 2007; McGowen and Szyf, 2010; Peedicayil, 2007; Petronis et al., 1999; McGowen and Szyf, 2010; Plazas-'M ayorca and Vrana, 2011; and Zawia et al., 2009).

A major challenge in the field includes the identification of an appropriate source material for home-based sample collection that is adequate for large-scale epigenetic research including whole-genome-analysis studies. Epigenetics may be the key for understanding the mechanisms of gene-environment interactions as growing evidence suggests that epigenetic mechanisms may provide a molecular memory of environmental experiences (Ho, 2010; Kappeler and Meaney, 2010; McGowen et al., 2009, McGowen and Szyf, 2010; Portela and Esteller, 2010; Richards, 2008; Russo et al., 2010; Tsai et al, 2010; and Vlaanderen et al., 2010). Preliminary data from some humans suggest that distinct methylation patterns in peripheral blood cells are associated with social behaviors including: childhood aggression, suicidal behaviors, and ageing (Kappeler and Meaney, 2010; McGowen et al., 2009; McGowen and Szyf, 2010; Portela and Esteller, 2010; Russo et al., 2010, Tierling et al., 2010; Tsai et al, 2010; and Zhang et al., 2011).

Due at least in part to the heterogeneous nature of human disease, particularly mental illness, and the complex interaction of contributing etiological factors, studies require large sample sizes to provide reliable and significant effects. However, current research options for sample collection for epigenetic studies do not meet this requirement of "large sample sizes." The need for large sample sizes for studies is also true in order to produce significant effects in regards to studying human-environment interactions as these interactions are also of a very complex nature with many contributing factors. The ability to perform large-scale "population sized" (subject samples numbering in at least the hundreds to thousands) epigenetic research can introduce a new understanding of human-environment interaction and facilitate the completion of longitudinal studies facilitating the development of epigenetic-based screening diagnostics crucial to the progression of modern medicine. This epigenetic research may lead to a new understanding of how the environment affects our epigenome and how this relates to a person's health outcome, which may further lead to the development of preventative interventions for individuals who are considered high-risk and diagnostics for these health disparities including, but not limited to, diagnosis.

Some epigenetic studies attempting to quantify environmental and other complex interactions in human populations use blood as the source material for experimentation. Blood can restrict the researcher's ability to conduct large population-sized studies as it:

1. generally requires medical supervision,
2. involves invasive procedures for collection,
3. carries stigma that limits participation, and
4. is expensive to collect and ship.

Naturally expressed bodily fluids, e.g., saliva and urine, can be an additional or alternative appropriate source material for home-based sample collection as they:

1. do not require invasive techniques,
2. do not have the same stigma as blood,
3. do not require professional supervision, and
4. can be inexpensive to collect.

In addition, at least saliva has been shown to contain white blood cells (Dos-Santos et al., 2009). The use of bodily fluids, e.g., saliva, urine, may enable large-scale "population-sized" epigenetic research. In addition, home-base sample collection of saliva, or urine, may allow for a much wider range of research options available as it can greatly increase participant numbers and samples can be more easily shipped by the subjects from anywhere in the world. For example, the ability to more easily ship samples from anywhere in the world can be particularly useful when samples are from countries that do not have laboratory infrastructure.

An organism's genome is a fixed sequence that contains its hereditary information and is the same in every cell of an organism. An organism's epigenome, by contrast, varies between cell types and changes over the organism's lifetime. Thus, epigenetic studies may include a single cell type as the source of sample material to control for these differences (Johnson and Tricker, 2010; Lister et al., 2009; and Rangwala et al., 2006). For example, human saliva contains numerous cell types, including epithelial cells, cells normally found in the blood (i.e., T-cells and B-cells), bacteria and debris (Dos-Santos et al., 2009 and Viet and Schmidt, 2008). The cells in saliva that are the most important to profile epigenetically are those that come from the blood stream, as these cells carry epigenetic information from the entire body (Kappeler and Meaney, 2010; McGowen and Szyf, 2010; McGowen and Szyf, 2010; Righini et al, 2007; Rosas et al., 2011, Vlaanderen et al., 2010 and Zhang et al., 2011).

Additionally, it may not be practical to use whole saliva DNA as the cells in saliva that are not found in the blood, such as epithelial cells, which make up the vast majority of cells in saliva (Dos-Santos et al., 2009) have the ability to "mask" the epigenetic effects seen in T-cells (cells that originated in the blood) by dampening the effect of the minority of cells (Dos Santos et al., 2009, Lister et al., 2009; and Tierling et al., 2010). To address these concerns AboGen developed a method to separate and extract the different cell types found in bodily fluids such as saliva by taking advantage of cell-specific markers and isolation techniques (e.g., magnetic). This method uses practical amounts of bodily fluids, such as saliva, to yield enriched cells that can be used for downstream biological applications including large-scale functional genomic studies (example epigenomic studies). For example, saliva sample processing technology allows collected samples to be processed into single cell types and have their epigenomes profiled.

Furthermore, saliva (and other bodily fluids) can present challenges with cell isolation as a source material for blood cells in respect to downstream experimentation for reasons such as:

1. Blood is a transporter fluid while saliva is a digestive fluid that can be rich in proteases, enzymes and secreted substances and urine is a excretory fluid consisting of unwanted waste products.
2. Some fluids can have a wide pH range and some of the pH values reported, such as for saliva, would result in death if blood reached that pH (saliva is 6.2-7.4; urine is 4.5-8; blood is 7.35-7.45).
3. Some fluids contain more bacteria than blood.
4. Some fluids contain non-cellular material that varies between individuals and interferes with cell isolation.
5. Some fluids include blood cells, such as T-cells, which can be abundant in blood, but may be rare in other naturally expressed bodily fluids, such as saliva or urine, and are vastly outnumbered by other cell types, such as epithelial cells, unlike in blood.
6. The subset of lymphocyte cells in some bodily fluids, such as saliva, greatly differs from the population of those cell types in blood. For example, only CD4+ CD8− T-cells are reported to be found in saliva.
7. Some fluids are produced each day, such as saliva at about a rate of 0.5-1.5 liters per day per person.

Therefore, there is a need for new methods for isolating rare cells (i.e., T-cells) from saliva and other naturally expressed bodily fluids.

For collecting saliva samples from a large population of people (example: functional genomic studies) who are widely geographically dispersed, several requirements may need to be met for an optimal sample collection device. For example, it may be beneficial to have the sample collection device securely house a toxic preservative solution in a closed chamber. Additionally, the sample collection device may be able to be sent to a donor with the toxic solution safely enclosed. The sample collection device may also allow easy and safe collection of a donor specimen, such as human saliva or urine, with no risk of exposure of the donor to the toxic solution. Furthermore, the sample collection device may allow the donor to safely mix the toxic solution and the specimen (for preservation of the specimen) with no risk of exposure of the donor to neither the toxic solution nor any other hazard. The sample collection device may also allow the donor to send the sample collection device to a laboratory for processing generally "as-is" after securely closing the sample collection device. Finally, the sample collection device may further allow a laboratory technician to receive the sample collection device and safely open it for processing with generally no risk of exposure to any hazards.

Some currently available sample collection devices include, for example, U.S. Pat. No. 7,482,116 which describes a device that utilizes disassociating a barrier to allow fluid communication between a cavity holding the donor sample and a solution, however, embodiments included in the patent are limited to the use of sharp extruding objects and thin pierceable membranes. The thin pierceable membranes can represent a safety hazard to the sample donor as any wrong manipulation (such as with a finger nail) can lead to piercing of the membrane and release of the solution. US patent publication no. 2009/0216213 A1 claims a device that utilizes a pierceable membrane to establish fluid communication between a cavity containing a solution and the donor sample. This can represent a safety hazard to the sample donor as any wrong manipulation can lead to piercing the membrane and exposing the solution. The device also requires exchange of the cap prior to sending the sample to the end user. This can represent a safety hazard as it may expose the sample donor to the potentially toxic solution. Therefore, there is a need for safer and easier to use sample collection devices.

Additionally, the purification process requires cells to maintain their antigen profiles and the epigenomic profiling requires that their epigenome be maintained. To this end, it is necessary to treat the cells in such a way that they are able to generally maintain these features. Currently available treatments generally do not meet this need. For example, U.S. Pat. Nos. 7,267,980 and 7,749,757 disclose solutions containing lysine, glycine and formaldehyde for stabilizing cells from blood. However, those solutions will not protect cells from proteases found in some bodily fluids, such as saliva. Therefore, there is a need for new solutions and methods that will preserve the antigenicity and epigenome of cells in other bodily fluids, such as saliva.

SUMMARY OF THE DISCLOSURE

Embodiments of the disclosure provide safer and easy to use sample collection devices for naturally expressed bodily fluids (for example), as well as solutions and methods for preserving cells of samples collected, and additionally, methods for isolating specific cells either collected and/or preserved. Such isolated cells (and even non-isolated collected cells), can then be analyzed for studies in any of: functional genomic and epigenetic studies, and biomarker discovery (for example).

The sample collection devices according to the present disclosure provide several advantages over currently available sample collection devices. For example, in some embodiments, the sample collection devices use a minimum amount of parts and do not require removal or exchange of a piece or an object thereof. In some embodiments, the sample collection devices do not require any additional manipulation by the sample donor apart from depositing the sample in the sample collection device and closing the sample collection device. In some embodiments, use of the sample collection devices provide improved safety for both the sample donor and the end user, since, for example, sharp objects are not included and there is limited to no risk of exposure to toxic solutions (e.g., sample preservative solutions).

In some embodiments of the sample collection device, the sample collection device can have two main mating bodies, a cap and a tube. The cap can include a closed cavity holding a preservative solution which can mate with the tube to constitute the closed sample collection device. The tube can be configured to receive the donor specimen. The cap and tube are configured so that when the donor deposits the specimen and closes the tube with the cap, the cavity holding the preservative solution may be opened to release the preservative solution and allow it to mix with the donor specimen.

In some embodiments, a bodily fluid sample collection device for the collection of naturally expressed bodily fluids is provided and includes a cap having an outer wall having an engagement member, and an interior chamber for holding a fluid. The chamber may comprise inner walls which define an interior space and an aperture, where the aperture is configured for sealing by a removable blocking member. The blocking member may include a first coupling member for engaging a corresponding second coupling member in a tube, thereby causing removal of the blocking member and opening of the aperture when the cap is coupled to the tube. The device also includes the tube which includes a containment wall defining a reservoir for bodily fluid sample collection, an engagement member complementary to the engagement member of the cap, and the second coupling member.

In some embodiments, one and/or another of the following features may be provided with a sample collection device:
 the removable blocking member is a disk-shaped member which threadably engages the aperture;
 the first coupling member comprises an indentation disposed centrally in the bottom of the blocking member and the second coupling member is disposed centrally within the tube;
 the first coupling member comprises a recess disposed eccentrically in the bottom of the blocking member and the second coupling member is disposed eccentrically within the tube;
 the removable blocking member comprises an annular member having threads arranged thereon, where the annular blocking member substantially covers the aperture, and the inner wall of the cap includes complementary threads, such that the annular member can be screwed into the interior space to uncover the aperture;
 a locking mechanism, to lock the cap to the tube (or lock any two components together), the locking mechanism may comprise a wedge and a complementary flange;
 a sealing mechanism which may comprise a sealing substance associated with the engagement member of the cap, where upon coupling the cap to the tube, the sealing substance flows into at least the engagement member of the cap;
 tamper-evident means for determining whether the cap has been opened, which may comprise a ring having a first portion thereof integral with an open end of the cap, where upon the cap being coupled to the tube, the ring is positioned adjacent the tube; as such, in some embodiments, upon the cap being de-coupled from the tube, the first portion is broken and the ring remains substantially adjacent the tube; and/or
 the fluid in the cap chamber comprises a solution for preserving cells.

In some embodiments, a bodily fluid sample collection device for the collection of naturally expressed bodily fluid is provided and includes a cap having an interior chamber for holding a fluid and a first engagement member, and a tube comprising a containment wall defining a reservoir for sample collection and a second engagement member for engagement to the first engagement member. In some such embodiments, the cap comprises an outer wall having the first engagement member, the chamber comprises inner walls defining an interior space which holds the fluid, and an aperture, the aperture being configured for sealing by a removable blocking member. In addition, in some embodiments, the blocking member includes a first coupling member for engaging a corresponding second coupling member of the tube, where upon the coupling of the cap to the tube, the blocking member is moved and the aperture opens.

In some embodiments, a method for collecting a sample of a naturally expressed bodily fluid (or toxic or hazardous fluid) is provided and includes providing a bodily fluid collection device according to any of the disclosed sample collection device embodiments, depositing the bodily fluid into the chamber, and mating the cap and tube together such that the corresponding engagement members engage, where the blocking member moves and the preservation fluid flows into the reservoir containing the bodily fluid such that cells contained in the bodily fluid are preserved for analysis. In some such embodiments, further steps may include at least one of (with reference to bodily fluids): isolating one or more cell types for a plurality of cell types in the bodily fluid, and analyzing the collected cells.

As one of skill in the art will appreciate, in some embodiments, at least one of DNA, RNA and proteins can be extracted from collected/preserved cells, whether the isolated cells, or non-isolated cells.

In some embodiments, a kit for the collection of naturally expressed bodily fluids (or toxic and/or hazardous fluids) is provided and comprises a plurality of sample collection devices according to of the disclosed sample collection devices.

In addition, the current disclosure relates to functional genomic studies including epigenetic studies. More particularly, this disclosure also relates to the isolation of cells from bodily fluids, such as saliva and urine, for these studies. Accordingly, some embodiments of the disclosure include methods for preserving the antigenicity and epigenome of cells, and isolating rare cells, including, without limitation T-cells from bodily fluids, such as saliva and urine, are disclosed herein.

As used herein, the collection of "bodily fluids" generally refers to the collection of naturally expressed bodily fluids (although some embodiments can be used for collection of intravenous collection methods—e.g., blood). Thus, with references to the disclosed embodiments, "bodily fluids" refer to naturally expressed bodily fluids including, for example, saliva and urine.

For example, in some embodiments, a solution for preserving cells in bodily fluids, such as saliva and urine, is provided for further separation into cell types and downstream analysis that allows for the cells in saliva to retain their antigenicity and cellular architecture during storage. The solution can contain at least one chemical fixing agent, such as but not limited to paraformaldehyde, and at least one protease inhibitor. In some embodiments, the solution may further contain, for example, one or more of: at least one antimicrobial agent, serum proteins from human and/or other animal species. The solution may be buffered at a pH between about 6.4 to about 8.4, and in some embodiments, between about 7.2 to about 7.6.

In some embodiments, a method for preserving cells in one or more bodily fluids includes contacting collected cells with a solution according to one and/or another embodiment of the present disclosure, which allows the cells to retain their antigenicity and epigenome, for example.

In some embodiments, a method for isolating cells from chemically fixed cells collected from a bodily fluid, e.g., saliva or urine, and includes centrifuging the cells to separate, for example, DNA and/or other soluble material from a pellet of cells, bacteria, and debris, enriching white blood cells from other contents of the pellet, and isolating specific cells (e.g., white blood cells) using antibodies conjugated to magnetic beads targeted to cell specific markers.

In some embodiments, methods for isolating a particular type of cell, for example, a type of white blood cell (e.g., lymphocytes), from one or more bodily fluids (e.g., saliva and/or urine), and includes one or more of the following steps (and, depending upon the embodiment, several or all of the following steps): providing a sample of bodily fluid comprising chemically fixed cells, optionally centrifuging the bodily fluid sample to obtain a pellet comprising cells, optionally re-suspending the pellet in a buffer, subjecting the re-suspended pellet to density gradient separation to obtain a layer of a mixture of white blood cell types (including lymphocytes), contacting the mixture of cell types with a solution containing specific binding agents for an epitope found on a particular type of white blood cell, and separating the particular type of white blood cell (including lymphocytes) from the mixture of white blood cell types.

In some embodiments, the specific binding agents may be magnetic beads coupled to antibodies specific to an epitope found on a particular type of white blood cell, and in the separation step may then comprise, for example, magnetically separating the particular type of white blood cell (including lymphocytes) from the mixture of white blood cell types (though other cell separation techniques are within the scope of the disclosure).

In some embodiments, the bodily fluid (e.g., saliva, urine) can be mixed with a chemical fixative solution and the mixture can be removed from the pellet. The pellet can then be re-suspended in a buffer. The re-suspended pellet may optionally be centrifuged and washed one or more times in the buffer. The washed pellet may then be applied to a hydrophilic polysaccharide mixture to form a gradient. This gradient may be different than that used for blood because the density of the cells in other bodily fluids (e.g., saliva, urine) after chemical fixation for preservation can be different due to the different density of the preserved cells requiring an alteration in the time, temperature, and/or density of the gradient for the cells to be processed through this density gradient.

Additionally, in some embodiments, the white blood cells can form a layer in the gradient. The white blood cell layer can be extracted from the gradient and placed in another centrifuge tube where it may be washed in a buffer and re-pelleted to remove the remaining gradient mixture. The pellet may then be re-suspended and incubated in a buffer containing antibodies that are conjugated to magnetic beads and specific to antigens that are specific for a cell type to be isolated. In some embodiments, the cell type to be isolated is T-cells and the antigen is a T-cell-specific antigen. In some embodiments, the antigen is CD4. The re-suspended cells in the buffer can be bound by the antibody and subjected to a magnetic field that magnetically attracts the cells bound to the antibody-conjugated magnetic beads to the side of the tube. Remaining liquid may then be removed from the tube and the tube is washed in buffer. Isolated T-cells then remain attracted to the side of the tube and are ready for further processing, such as freezing for later downstream experimentation (for example).

In some embodiments, a method for preserving cells in a naturally expressed bodily fluid comprises contacting the bodily fluid with the preservation solution according to any of the disclosed embodiments.

The devices, solutions and methods of sample collection, preservation, isolation and analysis will be better understood in light of the following drawings, detailed description and claims. Like reference symbols in the various drawings indicate like elements.

It is worth noting that while some embodiments of the sample collection devices disclosed herein are set forth for use with the collection of bodily fluids, the same also has particular use with the collection of any other substance, including hazardous and/or toxic fluids.

BRIEF DESCRIPTION OF THE DRAWINGS

FIG. 1 shows a sample collection device comprising a cap and a tube according to some embodiments of the present disclosure.

FIG. 2A shows a longitudinal cross section view of a sample collection device in which the cap contains an inner chamber with a removable blocking member that has an eccentrically located coupling feature which can mate with a coupling member eccentrically located in the tube according to some embodiments of the present disclosure.

FIG. 2B is a cross section view taken along line 2B-2B of FIG. 2A and shows a coupling member eccentrically positioned within the tube according to some embodiments of the present disclosure.

FIG. 6 shows a sample collection device further including a sealed cavity containing a sealing solution that is released into the engagement features of the cap and tube when the cap is coupled to the tube, which prevents the cap from being removed by at least the donor after the cap has been coupled to the tube according to some embodiments of the present disclosure.

FIG. 7A shows a "tamper-evident" cap, in which an annular member at the bottom of the cap can break away from the cap if the cap has been removed after having been rotated/screwed onto the tube according to some embodiments of the present disclosure.

FIG. 7B shows the "tamper-evident" cap shown in FIG. 7A showing the annular member broken away from the cap according to some embodiments of the present disclosure.

FIG. 8 shows the time course of DNA yield in samples stored in chemical fixative solution at room temperature after 0, 1, 2 and 7 days, as well as DNA extracted from T-cells from each sample according to some embodiments of the present disclosure.

DETAILED DESCRIPTION OF THE EMBODIMENTS

Figure 1A:
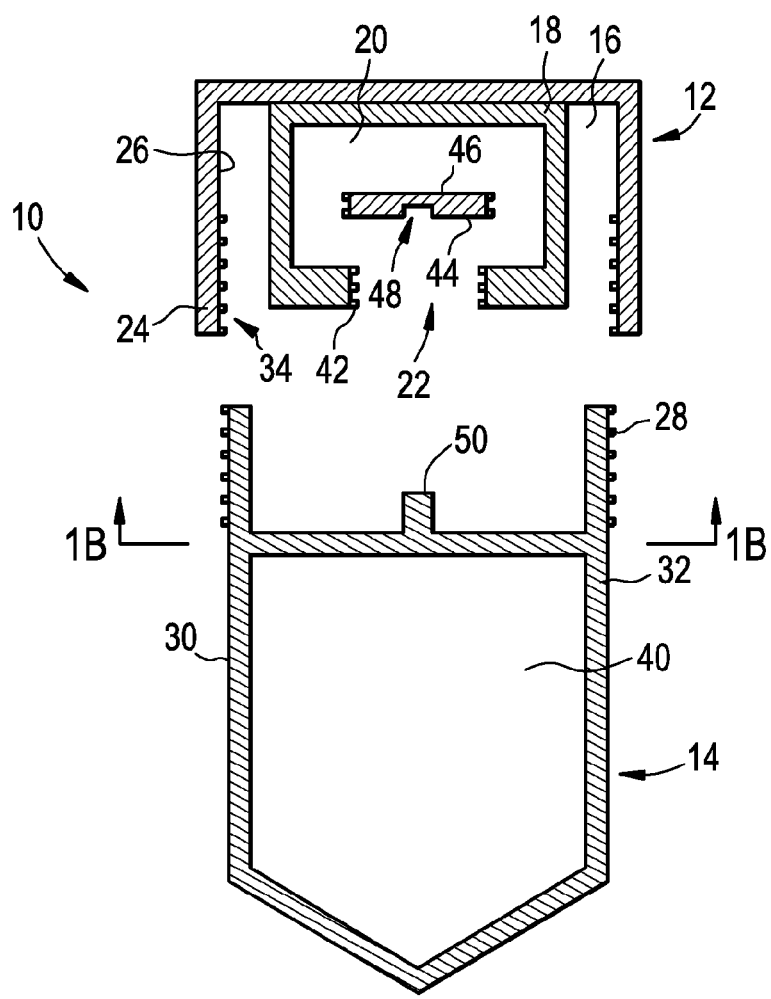
FIG. 1A is a cross section view taken along line 1A-1A of FIG. 1 and shows the interior chamber of the cap comprising inner walls which define an interior space and an aperture according to some embodiments of the present disclosure.

Embodiments of the present disclosure include devices, solutions and methods for the collection of samples, such as bodily fluids, as well as methods for isolating one or more cell types from collected cells (chemically fixed or otherwise). For example, in some embodiments, the sample collection devices provide several advantages over currently available sample collection devices, and in addition, the sample collection devices according to some embodiments use a minimum amount of parts and the devices do not require removal or exchange of a piece or an object. Furthermore, in some embodiments, the sample collection devices may generally not require additional manipulation by the sample donor apart from depositing the sample and closing the collection device. The sample collection devices according to some embodiments include improved safety of use for both sample donors and end users due, at least in part, to the elimination of sharp objects and limited risk of exposure to toxic solutions, as will be described in greater detail below.

In some embodiments, methods for the preservation and isolation of cells from bodily fluids for functional genomic and epigenetic studies, as well as biomarker discovery, are provided. Additionally, this disclosure provides devices, solutions and methods for isolating rare preserved cells, such as T-cells, from bodily fluids (i.e., saliva, urine), as will also be described in greater detail below.

Some embodiments of the sample collection device may include two mating bodies, such as a cap and a tube. In some embodiments, the cap may include a closed cavity, such as an interior space, for holding a preservative solution (which may be toxic) for mating with the tube to constitute a closed sample collection device. The tube may be configured to receive a donor specimen, such as one or more bodily fluids (e.g., saliva, urine). In some embodiments, the cap and/or tube may be configured so that when the donor deposits the specimen and closes the tube with the cap, the cavity in the cap, which may be holding the preservative solution, can be opened to release the preservative solution and allow it to mix with the donor specimen.

One of skill in the art will appreciate that with respect to some embodiments of the collection device described herein, such may be used in combination with accessories that ease specimen deposit within the collection device, including, for example, mouth adapters for saliva collection, funnels and hoses for urine collection, and the like.

In some embodiments, the sample collection device may comprise a cap having an outer wall with interior threads. Additionally, the sample collection device may include an interior chamber for holding a fluid with the chamber comprising walls defining an interior space and a threaded aperture in the wall. The aperture in the wall may be sealed by a threadably removable blocking member, where the blocking member may include engaging members for engaging a coupling member in a tube, thereby causing the blocking member to be removed and the aperture to open when the cap is threaded onto the tube (in some embodiments). In some embodiments, the sample collection device may further include a tube comprising a containment wall defining a lumen or reservoir for sample collection, exterior threads complementary to the interior threads of the outer wall of the cap, and a coupling member that has a shape which is complementary to the engaging member in the cap.

In some embodiments, the threadably removable blocking member can be a disk-shaped member that is at least one of pushed, rotated, screwed, threaded, and/or mated into the aperture of the inner chamber and can be at least one of pushed, rotated, screwed, threaded, and/or mated into the chamber by interaction between the engaging member of the cap and the coupling member of the tube when the cap is rotated or screwed onto the tube. The engaging member can be either centrally or eccentrically located in the disk-shaped member, with the coupling member being at least one of centrally or eccentrically located in the tube, respectively.

The terms push, rotate, screw, mate as well as thread, couple, and attach, as well as any corresponding tenses and plurals thereof (as additionally including the term "feature(s)), disclosed herein, correspond to structure (well known to those of skill in the art) for connection (either permanent or temporary) of two (or more) components (e.g., "screw means" "mating means", "coupling feature", "engagement feature"). For example, with respect to "pushing", such means can cover a "snap-fit" type of structure; rotation means can cover means in which a protruding member is received by a corresponding recess when one component is rotated relative to another. "Screwed" and "threadably" covers helical threaded engagement and the like. Thus, use of any of these terms (or tenses thereof) can also cover such connection with any such means or the equivalents thereof.

In some embodiments, a threadably movable annular member may not fit into the aperture, but rather covers the aperture from the outside of the inner chamber. In such embodiments, the annular member can have interior threads complementary to threads on the outside of the inner chamber or interior space. Interaction between the coupling features of the annular blocking member and the coupling member of the tube can cause the annular member to be screwed up the outside of the inner chamber, away from the aperture.

In some embodiments, the sample collection device may further include locking or sealing means, such that the cap cannot be removed from the tube by the donor once the cap has been connected or screwed onto the tube, such as by the donor. Suitable locking members can include a wedge on the cap and a matching flange on the tube or visa-versa. The wedge and flange can either be on the inside of the cap and tube, or on the outside of the cap and tube. Suitable sealing means include a sealed cavity containing a sealing solution, such as a glue, wherein the sealing solution is released when the cap is pushed, rotated or screwed onto the tube and thereafter cures in order to prevent disengagement between the cap and tube. In some embodiments, the sealing solution may be a two-component glue, such as an epoxy, with one component being sealed into the cap, and the other component sealed into the tube, such that the two components mix within the threads when the cap is screwed onto the tube. In other embodiments, the sealing solution can be a single component, such as a cyanoacrylate-based glue, which can be in a sealed cavity in the cap or tube, such that the sealing solution is released into the threads when the cap is screwed onto the tube. In some embodiments, the sealing solution can cure soon after engagement between the cap and tube such that disengagement between the tube and cap by the user can be generally prevented.

Alternatively, or in addition, some embodiments may further include an annular member at the base of the cap that is partially secured to the cap, such that removal of the cap after it has been screwed onto the tube breaks the bond between the cap and the annular member, thereby indicating that the tube has been opened. This "tamper-evident" embodiment is similar to those used to attach a cap to a soda bottle.

The sample collection devices according to some embodiments can be made of any suitable plastic, such as polypropylene, polystyrene and polycarbonate. The dimensions of the device can be modified to suit the specific processing the sample will be subjected to. In certain embodiments, typical dimensions include the following. For the inner chamber of the cap, the volume is from about 3 ml to about 10 ml, typically about 6 ml. For the lumen of the tube, the volume is from about 15 ml to about 50 ml, typically about 25 ml. Other volumes are within the scope of some embodiments of the present disclosure.

With respect to the figures, FIG. 1 is an illustration of an embodiment of a sample collection device 10 comprising a cap 12 and a tube 14. The tube can be configured for collection of one or more sample bodily fluids, and the cap can be configured for storing one or more preservation fluids. Additionally, the cap 12 and tube 14 can be configured to securely mate with one another in order to provide a secure containment of at least the sample bodily fluids for storing and shipping. Furthermore, the mechanism by which may be implemented in the sample collection device 10 for securely mating the cap 12 and the tube 14 may prevent disengagement between the cap 12 and the tube 14. One benefit of preventing disengagement between the cap 12 and the tube 14 is that it can prevent at least, for example, contamination of the sample contained in the tube and exposure of any preservation solutions (which may be toxic) to the sample donor, such as those contained in the cap 12.

FIG. 1A shows an example interior chamber 16 of the cap 12 which may be defined by at least one outer wall 24 and at least one inner wall 18 according to some embodiments. The at least one inner wall 18 may further define an interior space 20 and an aperture 22. In addition, the outer wall 24 may include one or more cap engagement features 34 along at least one side of the outer wall 24 for engaging the tube 14. For example, and shown in FIG. 1A, an inside surface 26 of the outer wall 24 can include one or more cap engagement features 34, such as threads, for engaging and mating with one or more complimentary tube engagement features 38, such as threads, associated with the tube 14. The tube 14 may be comprised of at least one containment wall 32 which may define a reservoir 40 for collecting and storing sample body fluids, such as saliva or urine. An outer surface 30 of the containment wall 32 may include the one or more tube engagement features 28, such as threads.

The cap 12 may further include an aperture 22 having one or more aperture engagement features 42, such as threads. In addition, the cap 12 may include a blocking member 46 which may have one or more blocking member engagement features 44, such as threads, for engaging the aperture engagement features 42. For example, the blocking member 46 may be removably coupled to the aperture 22 such that when the blocking member is secured to the aperture, one or more fluids or materials, may be contained within the interior space 20 of the cap. However, upon decoupling of the blocking member 46 to the aperture 22, the one or more fluids or materials may be released from the interior space 20 in the cap 12. For example, once the cap 12 has at least been partially secured to the tube 14, the blocking member 46 may be decoupled from the aperture 22, thereafter allowing fluids or materials in the interior space 20 to be released into the reservoir 40 of the tube 14. The one or more fluids or materials contained in the interior space 20 in the cap 12 may assist in preserving the sample body fluids contained in the reservoir 40 of the tube 14 during at least storage and shipping. Any of the engagement features discussed herein may be any number of engagement features for allowing temporary or permanent engagement between two parts or features of the sample collection device 10 and are not limited to the examples discussed in this disclosure.

The blocking member 46 may also include one or more coupling features 48 which may allow one or more coupling members 50 comprising a part of the tube 14 to engage and couple with the coupling features 48. The coupling between the coupling features 48 and coupling members 50 can assist in decoupling the blocking member 46 from the aperture 22. For example, as the cap 12 is secured to the tube 14, the coupling member 50 may engage and interact with the coupling feature 48 of the blocking member 46, such as similar to the head of a screw driver interacting with the head of a screw. The blocking member 46 may be threadably engaged with threaded aperture engagement features, and the coupling and interaction of the coupling feature 48 and coupling member 50 may cause the threaded engagement between the blocking member 46 and the aperture 22 to be released. The threaded engagement between the blocking member 46 and the aperture 22 may be released, for example, due to rotation of the blocking member 46 relative to the aperture 22. Any number of releasable engagements may be used to engage the blocking member 46 with the aperture 22 such that the engagement between the blocking member 46 and the aperture 22 may be released upon securing the cap to the tube 14. Similarly, any number of features may be integrated in the sample collection device 10 which may allow containment of a solution in a part of the cap 12 or tube 14 such that the solution is not released until the cap is at least partially secured to the tube 14.

Figure 1B:
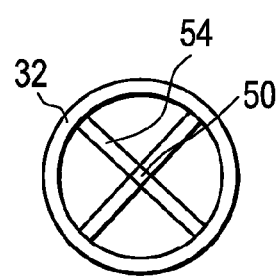
FIG. 1B is a cross section view taken along line 1B-1B of FIG. 1A and shows a coupling member centrally positioned within the tube according to some embodiments of the present disclosure.

The tube 14 in FIG. 1A is shown by way of example as having a coupling member 50 in the shape of a square peg which is complementary to a square shaped indent comprising the coupling feature 48 in the blocking member 46. Furthermore, the coupling member 50 can be centrally located within the tube 14 and the coupling feature may be centrally located on the bottom of the blocking member 46. Therefore, upon threaded engagement between the cap 12 and the tube 14, the square peg coupling member 50 may extend into and engage the square shaped indent coupling feature 48 in the blocking member 46, thus preventing the blocking member 46 from rotating relative to the coupling member 50. However, although the blocking member 46 may be prevented from rotating relative to the coupling member 50, the blocking member 46 may rotate relative to the aperture 22 and become disengaged from the aperture 22, such as from releasing the threaded engagement between the blocking member 46 and aperture 22. FIG. 1B shows an example coupling member 50 secured to an inner surface 52 of the containment wall of the tube 14 by more than one cross-member 54. The one or more cross members 54 can assist in securing the position of the coupling member 50 while allowing space for the passage of fluids or materials into the reservoir 40.

An example method of use of a sample collection device 10 can include the sample collection device 10 supplied with sample preservation fluid in the interior space 20 of the cap 12, and with the blocking member 46 threadably engaged with the aperture 22 in order to contain the sample preservation fluid in the interior space 20. Sample fluid, such as saliva or urine, may then be placed in the reservoir 40 of the tube 14 by a donor. The cap 12 can then be screwed onto the tube 14. Screwing the cap 12 onto the tube 14 may cause the coupling member 50 in the tube 14 to engage the coupling feature 48 of the blocking member 46 and unscrew the blocking member 48 from the aperture 22 and into the interior space 20 of the cap 12. Decoupling the blocking member 48 from the aperture 22 can allow the sample preservation fluid to flow into the reservoir 40 of the tube 40. After release of the sample preservation fluid into the reservoir 40 of the tube 14, the sample preservation fluid can mix with the donor's sample fluid, thereby preserving the donor's sample fluid.

While shown as a square peg in this illustration, the coupling member 50 of the tube 14 can be any shape that is complementary in shape with the coupling feature 48 of the blocking member 46 such that it allows the blocking member 46 to decouple from the aperture 22. The coupling feature 48 can be either in the blocking member 46 or the tube 14, and the complimentary coupling member 50 may be either in the tube 14 or blocking member 46, respectively. Other shapes will be evident to one skilled in the art, including, without limitation, a slot and a tab, like a regular screwdriver and screw, or a cross-shaped pair, like a Phillips screwdriver and screw.

An additional embodiment of the sample collection device 100 is shown by way of example in FIGS. 2A and 2B. The sample collection device 100 may include one or more coupling members 50 and complimentary coupling feature 48 which may be placed eccentrically from either the cap 12 or tube 14. As shown in FIG. 2B, less material and parts may be required for this embodiment to work properly, such as the coupling member 50 maintaining proper positioning by only one cross-member 54. Although the coupling member 50 is shown as being held in position by only one cross-member 54 extending from the containment wall 32 of the tube 14, any number of configurations and cross-members 54 may be used to position the coupling member 50 without departing from the scope of this disclosure.

Figure 3A:
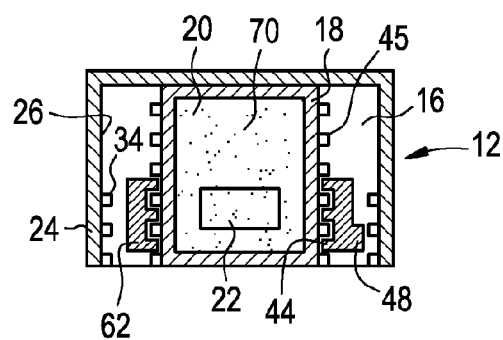
FIG. 3A shows an embodiment of the cap of the sample collection device in which the cap contains an inner chamber with a movable annular member that can cover an aperture in the inner wall according to some embodiments of the present disclosure.
Figure 3B:
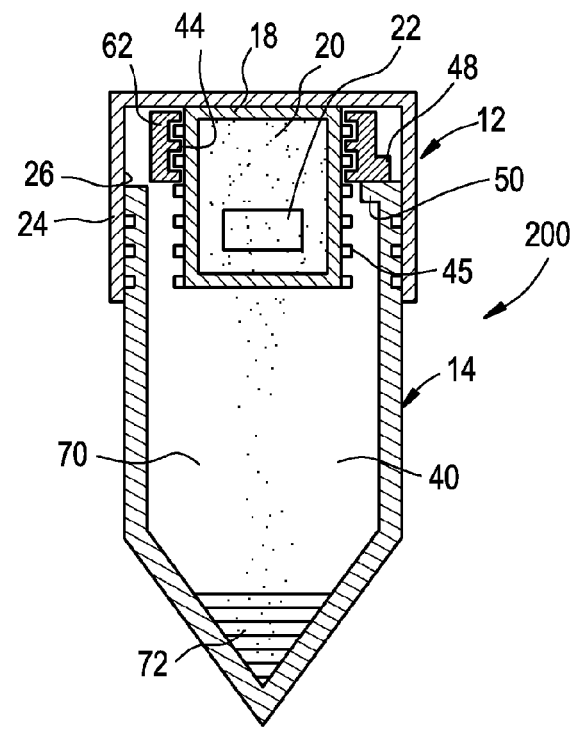
FIG. 3B shows an embodiment of the sample collection device in which the cap is coupled to the tube and the movable annular member is moved to a position where it does not cover an aperture in the inner wall according to some embodiments of the present disclosure.
Figure 3C:
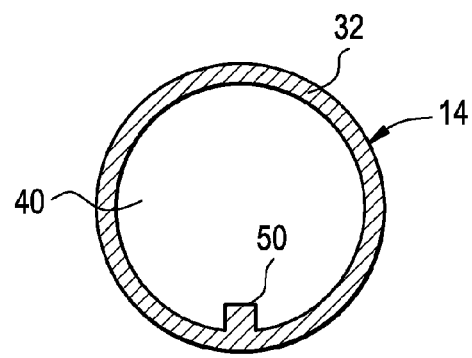
FIG. 3C is a top view of the tube shown in FIG. 2B and shows a coupling member positioned within the tube according to some embodiments of the present disclosure.

Another embodiment of the sample collection device 200 is shown by way of example in FIGS. 3A-3C. More specifically, FIG. 3A shows a cross section of the cap 12 prior to being coupled to the tube 14. The cap 12 can include an outer wall 24 and cap engaging members 34 along an inside surface 26 of the outer wall 24. The interior space 20 may be at least partially defined by at least one of an inner wall 18 or outer wall 24 of the cap 12. Furthermore, the inner wall 18 can include engagement features 60, such as threads, along a surface of the inner wall 18. The inner wall 18 may further define an aperture 22 which may be open or closed depending on the position of an annular blocking member 62 relative to the aperture 22. When the aperture 22 is closed such that the annular blocking member 62 is covering the aperture 22, fluid or material, such as sample preservation fluid or material 70, that may be contained in the interior space 20 may not be allowed to travel outside of the interior space 20, as shown in FIG. 3A. However, when the aperture 22 is open such that the annular blocking member 62 is not covering the aperture 22, the fluid or material 70 that may be contained in the interior space 20 may be allowed to travel outside of the interior space 20, such as into the reservoir 40 of the tube 14, as shown in FIG. 3B. The fluid or material 70 contained in the interior space may be beneficial for preserving sample 72, such as body fluids (i.e., saliva, urine, etc.) placed in the reservoir 40 of the tube 14, similarly as described above. Furthermore, any number of mechanisms may prevent the sample preserving fluid or material 72 from being released from the interior space 20 until the cap 12 is at least partially secured to the tube 14.

In the embodiment shown by way of example in FIGS. 3A-3C, the annular blocking member 62 may be configured to interact with one or more features, such as a coupling member 50, of the tube 14 such that as the cap 12 is being securely coupled to the tube 14, the one or more features of either the tube 14 or annular blocking member 62 can cause the annular blocking member 62 to move from a position where the annular blocking member 62 is covering the aperture 22 to a position where the annular blocking member 62 is not covering the aperture 22, thus allowing the sample preserving fluid or material 72 to release from the interior space 20 and interact with the sample 72.

FIG. 3C shows a cross section of the tube 14, having a containment wall 32 defining a reservoir 40 for sample collection. The tube 14 can include a coupling member 50 for engaging the coupling feature 48 of the annular blocking member 62.

An example method of use of a sample collection device 200 can include the sample collection device 200 supplied with sample preservation fluid 70 in the interior space 20 of the cap 12, and with the annular blocking member 62 covering the aperture 22 in order to prevent the passage of sample preservation fluid 70 through the aperture 22. In this embodiment, sample fluid 72, such as saliva or urine, can be placed in the reservoir 40 of the tube 14. The cap 12 may then be securely coupled, such as threadably engaged, onto the tube 14 causing the coupling features 48 of the annular blocking member 62 to engage the coupling member 50 of the tube 14. The annular blocking member 62 can then threadably engage the engagement features, such as threads, along the side of the inner walls. This can cause the annular blocking member 62 to move away from the aperture 22 so that it no longer covers the aperture 22. This, in turn, can release at least some of the sample preservation fluid 70 into the reservoir 40 of the tube 14, where it can mix with the sample fluid 72, thereby preserving it.

Figure 4A:
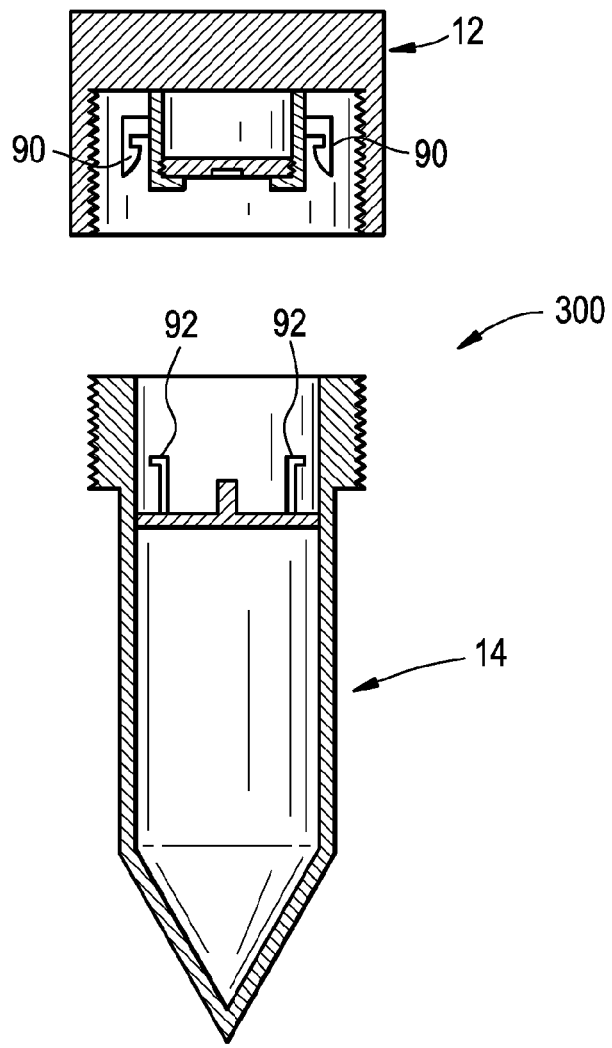
FIG. 4A shows an embodiment of the sample collection device comprising a locking mechanism disposed within the inside of the cap and the tube, which prevents the cap from being removed by at least the donor after the cap has been coupled to the tube according to some embodiments of the present disclosure.
Figure 4B:
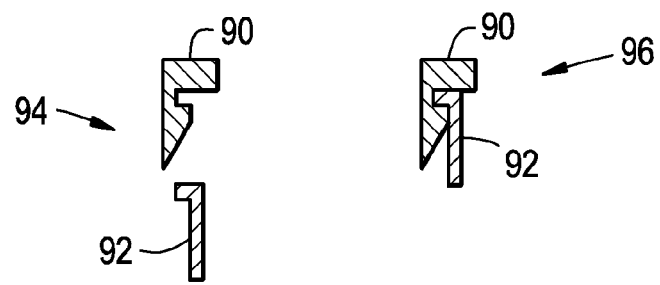
FIG. 4B shows the locking mechanism in the sample collection device shown in FIG. 4A showing a locked configuration and an unlocked configuration according to some embodiments of the present disclosure.

In some embodiments, the sample collection device 300, as shown by way of example in FIGS. 4A and 4B, cap 12 includes at least one coupling feature or a wedge 90 which is shaped and configured to interact with a complimenting coupling feature or a flange 92 of the tube 14. In this embodiment, the wedge 90 and flange 92 are extending along an inside surface of the cap 12 and tube 14. For example, when the cap 12 is coupled to the tube 14, the wedge 90 can engage the flange 92 and form a secure engagement between the cap 12 and the tube 14. Furthermore, once the wedge 90 and flange 92 have been completely engaged with each other, such as the locked configuration 96 shown by way of example in FIG. 4B, the engagement between the wedge 90 and the flange 92 may not be releasable by at least the sample donor. Therefore, once the cap 12 becomes engaged to the tube 14 such that the wedge 90 and flange 92 are securely engaged with each other, the cap 12 may no longer be disengaged from the tube 14 by at least the sample donor. This can prevent at least the sample donor from contaminating the sample body fluid that was deposited in the tube 14, as well as protect the sample donor from contact with the sample preservation solution. FIG. 4B shows sample embodiments of the unlocked configuration 94 and locked configuration 96 between the wedge 90 and flange 92.

Figure 5A:
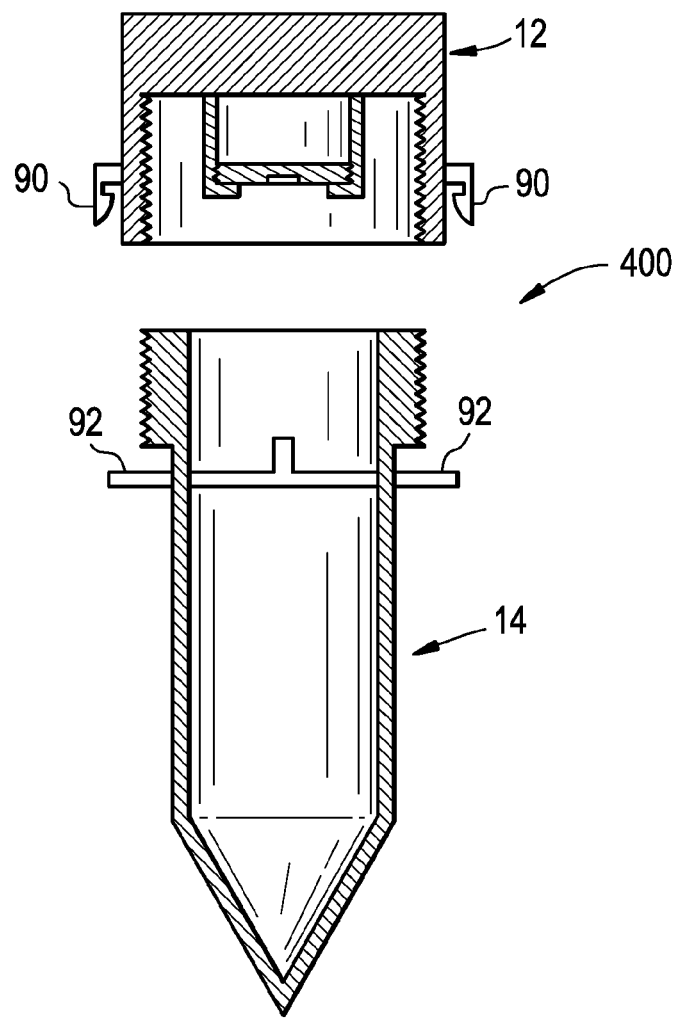
FIG. 5A shows a sample collection device comprising a locking mechanism disposed on an outer surface of the cap and tube, which prevents the cap from being removed by at least the donor after the cap has been coupled to the tube according to some embodiments of the present disclosure.
Figure 5B:
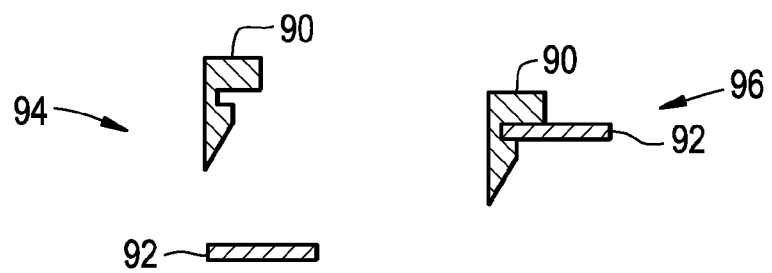
FIG. 5B shows the locking mechanism in the sample collection device shown in FIG. 5A showing a locked configuration and an unlocked configuration according to some embodiments of the present disclosure.

In some embodiments, the sample collection device 400, as shown by way of example in FIGS. 5A and 5B, the wedge 90 and flange 92 are extending along an outside surface of the cap 12 and tube 14, respectively. FIG. 5B shows sample embodiments of the unlocked configuration 94 and locked configuration 96 between the wedge 90 and flange 92.

In some embodiments, the sample collection device 500, as shown by way of example in FIG. 6, where the cap 12 includes one or more sealed cavities 110 containing a sealing substance 112, such as glue. Any one sealed cavity 110 may be either operatively associated or positioned adjacent engagement features 34, such as threads, on the cap 12 such that when the cap 12 is coupled to the tube 14 the one or more sealed cavities 110 may be broken by one or more features or end 150 of the tube 12. Once the sealed cavity 110 is broken, a sealing substance 112, such as glue, may be released from the sealed cavity 110 and cause the cap 12 to become permanently secured to the tube 14.

Any number of features may be included with the cap 12 or tube 14 which may assist in preventing unwanted decoupling of the cap 12 from the tube 14, such as to prevent contamination. Additionally or alternatively, either the cap 12 or tube 14 may include a "tamper evident" feature 160 which may become altered such that it can be known to a user or sample collector if the cap 12 has been unfavorably decoupled from the tube 14. As shown by way of example in FIGS. 7A and 7B, the cap 12 may include a tamper evident feature 160 which may be comprised of a ring that is releasably attached to the open end 162 of the cap 12 such that when the cap 12 is unfavorably decoupled from the tube 14, the tamper evident feature 160 can permanently release its attachment from the cap 12, as shown in FIG. 7B. Once the tamper evident feature 160 is permanently detached from the cap 12, any observer of the cap 12 can determine that the cap 12 had been unfavorably decoupled from the tube 12, thus providing a warning of sample contamination, for example.

Those skilled in the art will recognize that numerous equivalent embodiments can be used to obtain the benefits provided by the sample collection devices disclosed herein. For example, while this specification refers to certain elements being in the cap 12, and others in the tube 14, one skilled in the art would recognize that reversing the elements in the cap 12 to be in the tube 14 and vice-versa, would be an equivalent.

In some embodiments, a solution for preserving cells in one or more bodily fluids, such as saliva and urine, is disclosed. The solution for preserving cells may be beneficial for further separation into cell types and downstream molecular analysis that allows for storage of cells in the body fluid to retain their antigenicity and cellular architecture. The solution may contain at least one chemical fixing agent, such as but not limited to paraformaldehyde, and at least one protease inhibitor. In some embodiments, the solution may further contain one or more of at least one antimicrobial agent, and serum proteins from human and/or other animal species. The solution can be buffered at a pH from between about 6.4 to about 8.4, preferably from between about 7.2 to about 7.6.

For purposes of the disclosure, "preserving cells" means preventing the cells from having their antigens degraded, such that they can be purified or enriched based on their antigens, and preventing alterations in the cellular epigenome. The "epigenome" means the state or pattern of alteration of genomic DNA by covalent modification of the DNA or of proteins bound to the DNA. Examples of such alteration include methylation at the 5 position of cytosine in a CpG dinucleotide, acetylation of lysine residues of histones, and other heritable or non-heritable changes that do not result from changes in the underlying DNA sequence.

In some embodiments, concentrations of agents in the following description can be those of the sample preserving solution itself. Depending upon the bodily fluid, and in the case of saliva, about an equal volume of solution and body fluid can be mixed together. This preferably results in the cells from the body fluids retaining their antigenicity and DNA integrity for at least one week at room temperature.

In some embodiments of the disclosure, the volume of preservation solution held within the device and deployed may be between about 100 and about 500 ml, which is relevant, for example, for the preservation of cells in urine. As such, the preservation solution for urine may be anywhere between about ten times (10×) concentrated solution to a one-point five time (1.5×) solution for urine.

A "chemical fixing agent", according to some embodiments, is a chemical cross-linking compound used to alter cell components such that the cells resist degradation. The chemical fixing agents can also serve to cross-link histones and other DNA-binding proteins to the DNA. Such agents may be known in the art and include, without limitation, paraformaldehyde, formaldehyde, formalin, aldehydes, alcohol, oxidizing agents, Mercurials, Picrates, Hepes-glutamic acid buffer-mediated organic solvent protection effect (HOPE), fixative combinations such as Zambonis fixative, combinations of aldehydes, and synthetic cross-linking reagents. In some embodiments, the chemical fixing agent is paraformaldehyde. In some embodiments, the chemical fixing agent is present at a concentration of about 1% (v/v).

To protect the cells from degradation by proteases present in the body fluids, in some embodiments, the solution can contain at least one protease inhibitor. In some embodiments, the protease inhibitor can be selected from the group consisting of Aspartic protease inhibitors, Cysteine protease inhibitors, Metalloprotease inhibitors, Serine protease inhibitors (e.g., serpins), Threonine protease inhibitors, Trypsin inhibitors, and Kunitz STI protease inhibitor. Some specific, non-limiting, examples include sodium azide, PMSF, Aprotinin, leupeptin, pepstatin, natural or synthetic proteinase inhibitors, and cocktail mixtures of protease inhibitors. Suitable concentrations of these inhibitors can include, without limitation, PMSF (Phenylmethylsulfonyl fluoride) Serine proteases at about 0.1-1 mM, Benzamidine Serine proteases at about 1 mM, Pepstatin A Acid proteases at about 1 μg/ml, Leupeptin Thiol proteases at about 1 μg/ml, Aprotinin Serine proteases at about 5 μg/ml, and Antipain Thiol proteases at about 1 μg/ml. In certain embodiments, the protease inhibitor is sodium azide at a concentration of about 0.01% (w/v).

To prevent damage to the cells from microbial contamination, some embodiments of the solution contain at least one antimicrobial agent. Suitable antimicrobial agents include, without limitation, antibacterial and antifungal antibiotics.

Preservation of cell architecture is enhanced by the presence of serum proteins, which may optionally be added to the solution in some embodiments. Additionally serum proteins may be used to neutralize osmotic difference between cells and solution. These can be from human or other animal sources. In some cases, whole serum may be used. For example, fetal bovine serum may be added, in some embodiments at about 1% (v/v).

The solution according to the disclosure may include any combination of the foregoing embodiments.

In some embodiments of the disclosure, a method for preserving cells in one or more bodily fluids is disclosed. The method for preserving the cells can comprise contacting the body fluids with the solution according to the present disclosure. The body fluids can contain a variety of cell types and the cells in the body fluids can be preserved by the solution according to the present disclosure. While not critical to the present disclosure, a ratio of solution to body fluids of from about 1 to 1 is typically used.

The following examples are intended to further illustrate some embodiments of the solutions and methods for preserving cells in body fluids and are not to be construed to limit the scope of this disclosure.

For example, a solution of PBS pH 7.4, 1% Paraformaldehyde, 1% FBS, and 0.01% NaN3 can be added at a 1:1 ration with saliva, then T-cells can be purified and DNA extracted. The results of such a process are shown in FIG. 8. These results can demonstrate that the integrity of the antigenicity and DNA of T-cells was maintained for at least one week.

In some embodiments of the present disclosure, a method is disclosed which provides a sample of one or more body fluids, such as saliva or urine, comprising chemically fixed cells, and optionally centrifuging the body fluid sample to separate DNA and other soluble material from a pellet of cells including bacteria and debris. The method can further include enriching white blood cells, including lymphocyte cells, from other contents of the pellet. Additionally, specific cells may be isolated using antibodies conjugated to magnetic beads targeted to cell specific markers.

In some embodiments, the disclosure provides a method for isolating a particular type of white blood cell, specifically including, but not limited to lymphocytes, from bodily fluids (i.e., saliva, urine, etc.), comprising, for example one or more (and in some embodiments, several or all of the steps): providing a body fluid sample comprising chemically fixed cells, optionally centrifuging the body fluid sample to obtain a pellet comprising cells, optionally resuspending the pellet in buffer, subjecting the re-supended pellet to density gradient separation to obtain a layer of a mixture of white blood cell types (including lymphocytes), contacting the mixture of cell types with a solution containing specific binding agents for an epitope found on a particular type of white blood cell, and separating the particular type of white blood cell (including lymphocytes) from the mixture of white blood cell types.

In some embodiments, the specific binding agents can include magnetic beads coupled to antibodies specific to an epitope found on a particular type of white blood cell, and separating may comprise magnetically separating the particular type of white blood cell (including lymphocytes) from the mixture of white blood cell types, though any method (and corresponding system/device) for separating cell types from one another is within the scope of this disclosure. Magnetic separation is but one method for doing so.

The cells can be chemically fixed prior to being subjected to the method according to this disclosure. The cells can be chemically fixed by, e.g., contacting a sample of saliva with a chemical fixation solution. This is done to preserve the cells over time at ambient temperatures. This can also allow for a complete study of the epigenome as it allows histone modifications and other protein-DNA interactions to be studied from the deposited body fluid samples. Histones must be chemically fixed to the DNA in order to be studied. Without fixation, the histones generally cannot remain bound to the DNA and the proteins can degrade over time.

In some embodiments, the buffer can comprise sodium azide, the buffer can comprise phosphate buffered saline and sodium azide, In some embodiments, the buffer may further comprise fetal bovine serum. In some embodiments, the buffer is at a pH from between about 7.2 to about 7.6.

In some embodiments, the cells are washed once in buffer. This in practice removes soluble material and in the case of saliva it removes what has been classified as the "buccal" layer (Dos-Santos et al., 2009).

In some embodiments, the mixture of white blood cells is washed one or more times in buffer prior to separating. This is preferably done to remove any remaining density gradient solution from the mixture of cell types.

In the process, the antibodies may bind to the particular type of white blood cells, thus binding the particular type of white blood cells to the magnetic beads. The particular type of white blood cells can then be separated from any other cell types by placing the magnetic beads in a magnetic field and removing any remaining liquid to obtain isolated cells of the particular type of white blood cells.

In some embodiments, the particular type of white blood cells can be a lymphocyte, where the lymphocyte may be a T-cell. In such embodiments, the antibodies used may be specific to an antigen specific to T-cells (e.g., the antigen being CD4). In some embodiments, the isolated blood cells may then be frozen prior to further processing, such as prior to epigenetic analysis.

The following example is intended to further illustrate an example method embodiment of the present disclosure and is not intended to limit the scope of the disclosure.

Example: Isolating T-cells from a bodily fluid (e.g., saliva)

Saliva is collected, and the saliva is mixed with preservation solution. The cells are then pelleted by centrifugation and the processing solution is removed. The cells are then re-suspended in about 6 ml buffer (PBS, pH 7.4), 1% FBS, 0.01% NaN3), then washed once in a buffer and repelletted. The pellet are resuspended in about 6 mL PBS-15 FBS-0.01% NaN3 and subjected to density gradient centrifugation using 1.082-1.072 g/ml of Ficoll® (GE Healthcare). The white-blood cells are spun to the interface of the polysaccharides and buffer while the bacteria, debris, and any other particulate matter were pelleted at the bottom of the tube. The cells are extracted from the tube and placed in a new tube. The cells are then washed in Hank's Balanced Salt Solution once and then washed with the PBS-NaN3-FBS buffer once to remove remaining density gradient solution that may have been taken while extracting the white blood cells from the interface.

Figure 9:
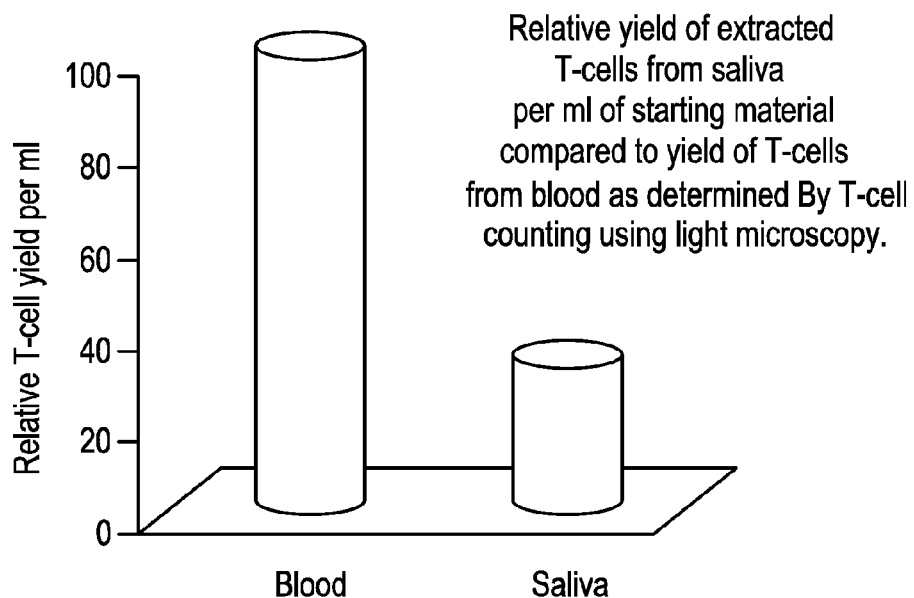
FIG. 9 is a chart illustrating the relative yield of extracted T-cells per ml of starting material (e.g., sample of bodily fluid), as compared to a yield of T-cells from blood.
Figure 10:
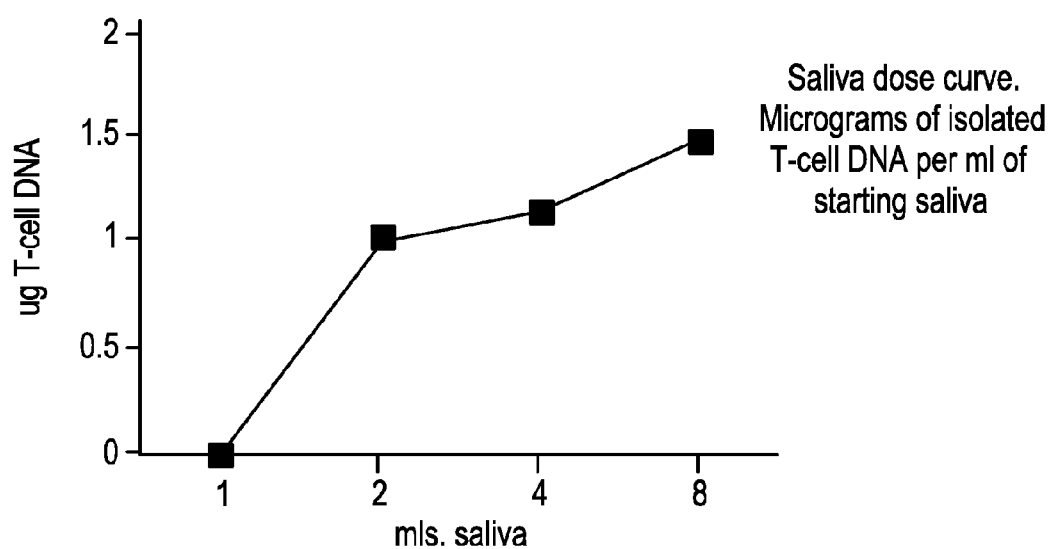
FIG. 10 shows a saliva dose curve of micrograms of isolated T-cell DNA per ml of saliva according to some embodiments of the present disclosure.

The sample now includes highly enriched white-blood cells with minimal bacteria and minimal debris. This step can also greatly decrease other cell types, such as epithelial cells. The cells can then be incubated in buffer (PBS-NaN3-FBS) with antibody targeted against CD4 conjugated to magnetic beads (Dynabeads® Invitrogen®). The samples can then be placed in a magnetic field, the beads brought to the side of the tube, and the liquid removed. The liquid may contain everything not bound to the beads through the antibody. The T-cells can be bound to the antibody and not removed due to the magnetic field. The beads and the attached cells can be washed in buffer to eliminate any non-specific or weak binding of other cells, bacteria, or other debris found in bodily fluids, such as saliva or urine. The cells can then be frozen for later downstream processing and analysis. The isolation of T-cells can be confirmed by light microscopy (T-cells are very distinct compared to epithelial cells and bacteria) (see FIG. 9). Additionally, flow cytometry and F.A.C.S. analysis using antibodies against CD3, CD4, and CD8 can confirm visual assessment of the isolated cells. The T-cells may then be tittered from the body fluid to determine the number of T-cells per unit of body fluid (ml) in order to determine the amount of body fluid, such as saliva or urine, for an adequate number of cells for downstream experimentation (see FIGS. 9 and 10). The isolated cells can be shown to have DNA devoid of degradation and appropriate for downstream use (see FIG. 8).

Any and all references to publications or other documents, including but not limited to, patents, patent applications, articles, webpages, books, etc., presented in the present application, are herein incorporated by reference in their entirety.

Although a few variations have been described in detail above, other modifications are possible. For example, any logic flow depicted in the accompanying figures and described herein does not require the particular order shown, or sequential order, to achieve desirable results. Other implementations may be within the scope of at least some of the following exemplary claims.

Example embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any and all elements from any other disclosed methods, systems, and devices, including any and all elements corresponding to collection, preservation, separating and isolating of cells from bodily fluids (e.g., saliva, urine), as well as the collection of other substances, including toxic and/or hazardous substances/fluids (as well as the preservation, separating and isolation of components thereof). In other words, elements from one or another disclosed embodiments may be interchangeable with elements from other disclosed embodiments.

REFERENCES HEREIN INCORPORATED BY REFERENCE

Abdolmaleky, H. M., Thiagalingam, S., Wilcox, M. (2005). Genetics and epigenetics in major psychiatric disorders: dilemmas, achievements, applications, and future scope. American Journal of Pharmacogenomics. 5(3):149-60.

Alika K. Maunakea, Iouri Chepelev, Keji Zhao. 2010. Epigenome Mapping in Normal and Disease States. Circ. Res. 107; 327-339

BCC Research. Cell-based assays: Technologies and global markets. 2011. market report BCC Research. Epigenomics. 2010. market report BCC Research. Life science tolls and reagents. 2011. market report BCC Research, Sample preparation in genomics, proteiomics, and epigenomic: global markets. 2011. market report Becker, M. A., & Dos-Santos, M. C. (2010). Psychological stress and its influence on salivary flow rate, total protein concentration and IgA, IgG and IgM titers. Neuroimmunomodulation. 17(6):396-404.

Bertho, A. L. 2009. Cell Phenotyping in saliva of individuals under phycological stress. Cellular immunology. 260:39-43.

Burdge, G. C., & Lillycrop, K. A. (2010). Nutrition, Epigenetics, and Developmental Plasticity: Implications for Understanding Human Disease. Annu. Rev. Nutr. 30:315-39.

Chouliarasa, L., Ruttena, B. P., Kenisa, F., Peerboomsa, O., Vissera, P. J., Verheya, F., van Osa, J., Steinbuscha, H. W., & van den Hovea, D. L. (2010). Epigenetic regulation in the pathophysiology of Alzheimer's disease. Progress in Neurobiology. 90(4): 498-510.

Costa, E., Grayson, R. D., & Guidotti, A. (2003). Epigenetic downregulation of GABAergic function in schizophrenia: Potential for pharmacological intervention. Molecular Interventions. 3(4): 220-229.

Dos-Santos M C, Matos-Gomes N, Makimoto F H, Katsurayama M, Santana L L, Becker M A, Paredes-Garcia E, Bertho A L. (2009). Cell Phenotyping in saliva of individuals under phycological stress. Cellular immunology. 260:39-43

Eaves, L., Silberg, J., Erkanli, A. (2003). Resolving multiple epigenetic pathways to adolescent depression. Journal of Child Psychology and Psychiatry. 44(7): 1006-1014.

Ho, S. (2010). Environmental epigenetics of asthma: An update. The Journal of Allergy and Clinical Immunology. 126(3):453-465.

Iwamoto, K., & Kato, T. (2009). Epigenetic Profiling in Schizophrenia and Major Mental Disorders. Neuropsychobiology. 60(1): 5-11.

Johnson L J and Tricker P J. (2010) Epigenomic Plasticity Within Populations: its evolutionary significance and potential. Heredity. 105: 113-121

Kalorama Information. Personalized medice diagnostics. 2011. market report

Kappeler, L., & Meaney, M. J. (2010). Epigenetics and parental effects. Bioessays. 32: 818-827.

Kuratomi G, Iwamoto K, Bundo M, Kusumi I, Kato N, Iwata N, Ozaki N, Kato T. (2007). Aberrant DNA methylation associated with bipolar disorder identified from discordant monozygotic twins. Mol. Psychiatry. 13(4): 429-441.

Lal R., Edison L., and Chused T., (1987). Fixation and long-term storage of human lymphocytes for surface marker analysis by flow cytometry. Cytometry 9:213-219

Lister, L., Pellizzola, M., Dowen, R. H, Hawkins, R. D., Hon, G., Tonti-Filipinni, N., et al. (2009). Human DNA methylome at base resolution show widespread epigenetic differences. Nature. 462: 315-322.

Matos-Gomes, N., Katsurayama, M., Makimoto, F. H., Santana, L. L., Paredes-Garcia, E., Mastroeni, D., Grover, A., Delvaux, E., Whiteside, C., Coleman, P. D., & Rogers, J. (2010). Epigenetic changes in Alzheimer's disease: Decrements in DNA methylation. Neurobiology of Aging. 31(12): 2025-2037.

McGowan, P. O. & Kato, T. (2007). Epigenetics in mood disorders. Environmental Health and Preventive Medicine. 13(1): 16-24.

McGowen, P. O., Sasaki, A., D'Alessio, A. C., Dymov, S., Labonte, B., Szyf, M., Turecki, G., Meaney, M. (2009). Epigenetic regulation of the glucocorticoid receptor in human brain associated with childhood abuse. Nature Neuroscience. 12(3):342-8.

McGowan, P. O., Szyf, M. (2010). The epigenetics of social adversity in early life: Implications for mental health outcomes. Neurobiology of Disease. 39: 66-72.

Mill, J., Petronis, A. (2007). Molecular studies of major depressive disorder: the epigenetic perspective. Molecular psychiatry. 12: 799-814.

Peedicayil, J. (2007). The role of epigenetics in mental disorders. Indian J Med Res. 126: 105-111.

Petronis, A., Paterson, A. D., & Kennedy, J. (1999). Schizophrenia: An epigenetic puzzle? Schizophr Bull. 25(4): 639-655

Plazas-Mayorca M, Vrana K. (2011). Proteomic investigation of epigenetic in neuropsychiatric disorders: A missing link between genetics and behavior? J Proteome Research. 10: 58-65

Portela A, and Esteller, M. 2010. Epigenetic modifications and human disease. Nature Biotechnology. 28:10, 1057

Righini C A, Fraipont F, Timsit J F, Faure C, Brambilla E, Reyt, Favrot M C. (2007). Tumor-specific methylation in saliva: A promising biomarker for early detection of head and neck cancer recurrence. Clin. Cancer Res. 13(4): 1179-85

Rosas S L B, Koch w, Carvalho M G C, Wu L, Califano J, Westra W, Jen J, and Sidransky D. (2001). Promoter hypermethylation patterns of p16, O-methylguanine-DNA-methyltransferase, and death associated protein kinase in tumors of and saliva of head and neck cancer patients. Cancer Research. 61:939-42

Russo P, Lauria F, Siani A. (2010) Heritability of body weight: Moving beyond genetics. Nutrition, Metabolism and Cardiovascular Diseases. 20: 691-697

Teirling S, Souren N Y, Reither S, Zang K D, Meng-Henschel J, Leitner D, Oehl-Jaschkowits B, Walter J. (2010). Dna methylation studies on imprinted loci in male monozygotic twin pairs discordant for Beckwith-Wiedmann syndrome. Clinical Genetics. 79: 1399-004

Tsai S J, Hong C J, Liou Y J. (2010). Recent molecular genetic studies and methodological issues in suicide research. Progress in neuro-psychopharmacology and biology psychiatry Viet C T, and Schmidt B L. (2008). Methylation Array Analysis of Preoperative and Postoperative Saliva DNA in Oral Cancer Patients. Cancer Epidemiol Biomarkers Pre. 17(12): 3603-11

Zhang F F, Cardarelli, Carroll J, Zhang S, Fulda K, Gonzales K, Vishwanatha J, Morabia A, Santella R. (2011). Physical activity and global methylation in a cancer-free population. Epigenetics. 6(3) 293-299

Vlaanderen, J., Moore, L. E., Smith, M. T., Lan, Q., Zhang, L., Skibola, C. F., Rothman, N., & Vermeulen, R. (2010). Application of OMICS technologies in occupational and environmental health research; current status and projections. Occup Environ Med. 67:136-143.

What is claimed is:

1. A bodily fluid sample collection device for the collection of naturally expressed bodily fluids, the device comprising:
a cap comprising:
an outer wall having an engagement member,
an interior chamber for holding a fluid, the chamber comprising an inner wall defining an interior space and an aperture;
a threadedly removable blocking member attached to and configured for sealing the aperture, wherein:
the blocking member includes a first coupling member for engaging a corresponding second coupling member in a tube when coupled thereto, and
upon the action of coupling the cap to the tube, the blocking member is threadedly removed from the aperture;
and
the tube, comprising:
a containment wall defining a reservoir for bodily fluid sample collection, an engagement member complementary to the engagement member of the cap, and the second coupling member.

2. The sample collection device according to claim 1, wherein the removable blocking member is a disk-shaped member which threadably engages the aperture.

3. The sample collection device according to claim 2, wherein the first coupling member comprises an indentation disposed centrally in the bottom of the blocking member and the second coupling member is disposed centrally within the tube.

4. The sample collection device according to claim 2, wherein the first coupling member comprises a recess disposed eccentrically in the bottom of the blocking member and the second coupling member is disposed eccentrically within the tube.

5. The sample collection device according to claim 1, wherein the device further comprises a locking mechanism.

6. The sample collection device according to claim 5, wherein the locking mechanism comprises a wedge and a complementary flange.

7. The sample collection device according to claim 1, wherein the device further comprises a sealing mechanism.

8. The sample collection device according to claim 7, wherein the sealing mechanism comprises a sealing substance associated with the engagement member of the cap, wherein upon coupling the cap to the tube, the sealing substance flows into at least the engagement member of the cap.

9. The sample collection device according to claim 1, further comprising tamper-evident means for determining whether the cap has been opened.

10. The sample collection device according to claim 9, wherein the tamper-evident means comprises a ring having a first portion thereof integral with an open end of the cap, wherein upon the cap being coupled to the tube, the ring is positioned adjacent the tube.

11. The sample collection device according to claim 10, wherein upon the cap being de-coupled from the tube, the first portion is broken and the ring remains substantially adjacent the tube.

12. The sample collection device according to claim 1, wherein the fluid comprises a solution for preserving cells.

13. The sample collection device according to claim 1, wherein the inner wall of the interior chamber is threaded for corresponding engagement with the threadedly removable blocking member.

14. The sample collection device according to claim 1, wherein the aperture of the interior chamber is threaded for corresponding engagement with the threadedly removable blocking member.

* * * * *